(12) United States Patent
Sahatjian et al.

(10) Patent No.: US 7,371,257 B2
(45) Date of Patent: *May 13, 2008

(54) STENT LINING

(75) Inventors: Ronald A. Sahatjian, Lexington, MA (US); James J. Barry, Marlborough, MA (US); Maria Palasis, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 515 days.

This patent is subject to a terminal disclaimer.

(21) Appl. No.: 10/997,088

(22) Filed: Nov. 23, 2004

(65) Prior Publication Data

US 2005/0090891 A1  Apr. 28, 2005

Related U.S. Application Data

(63) Continuation of application No. 10/059,420, filed on Jan. 31, 2002, now Pat. No. 6,890,339, which is a continuation of application No. 09/129,280, filed on Aug. 5, 1998, now Pat. No. 6,364,893, which is a continuation of application No. 08/717,290, filed on Sep. 20, 1996, now Pat. No. 5,843,089, which is a continuation-in-part of application No. 08/507,844, filed on Jul. 27, 1995, now Pat. No. 5,685,847, which is a continuation-in-part of application No. 08/268,999, filed on Jun. 30, 1994, now Pat. No. 5,439,446, said application No. 08/717,290 is a continuation-in-part of application No. 08/097,248, filed on Jul. 23, 1993, now Pat. No. 5,674,192, which is a continuation-in-part of application No. 07/795,976, filed on Nov. 22, 1991, now Pat. No. 5,304,121, which is a continuation-in-part of application No. 07/635,732, filed on Dec. 28, 1990, now abandoned, which is a continuation-in-part of application No. 07/451,507, filed on Dec. 15, 1989, now Pat. No. 5,135,516.

(51) Int. Cl.
*A61F 2/06* (2006.01)
(52) U.S. Cl. .................................. 623/1.46; 427/2.24
(58) Field of Classification Search ............... 623/1.11, 623/1.44, 1.46, 1.18; 427/2.24, 2.25, 2.28, 427/2.3, 261, 286, 287; 606/192, 194, 198
See application file for complete search history.

(56) References Cited

U.S. PATENT DOCUMENTS 2,329,456 A    9/1943  Campbell (Continued)

FOREIGN PATENT DOCUMENTS

CA            215597        12/1986

(Continued)

OTHER PUBLICATIONS

Abstract 680, "The In Vivo Effectiveness of Heparin Bonding of Catheters Using Indium 111 Labelled Platelets", Abstracts from Circulation, vol. 62, Supp. III, Oct. 1980.

(Continued)

*Primary Examiner*—Kevin T. Truong
(74) *Attorney, Agent, or Firm*—Kenyon & Kenyon LLP

(57) ABSTRACT

The invention features a catheter assembly and methods for delivering a hydrogel-lined stent to a body lumen, and methods for lining a stent with a hydrogel. The assembly includes a catheter which has a balloon at least a portion of which is coated with a hydrogel and an expansible stent mounted on the balloon in a contracted condition for passage with the catheter to a site of a body. Expansion of the balloon lodges the stent in the body with hydrogel coated on the inner surfaces of the stent as a lining.

47 Claims, 3 Drawing Sheets

U.S. PATENT DOCUMENTS

| | | |
|---|---|---|
| 2,911,321 A | 11/1959 | Herrmann |
| 3,005,728 A | 10/1961 | Bridgeford |
| 3,023,126 A | 2/1962 | Underwood |
| 3,092,512 A | 6/1963 | Magat |
| 3,198,692 A | 8/1965 | Bridgeford |
| 3,216,983 A | 11/1965 | Shalanski |
| 3,304,353 A | 2/1967 | Harauteneian |
| 3,457,098 A | 7/1969 | Leininger |
| 3,566,874 A | 3/1971 | Shepherd et al. |
| 3,634,123 A | 1/1972 | Eriksson |
| 3,695,921 A | 10/1972 | Shepherd et al. |
| 3,810,781 A | 5/1974 | Eriksson |
| 3,812,071 A | 5/1974 | Stoy et al. |
| 3,844,989 A | 10/1974 | Harumiya et al. |
| 3,846,353 A | 11/1974 | Grotta |
| 3,861,396 A | 1/1975 | Vaillancourt |
| 3,935,342 A | 1/1976 | Lim |
| 3,975,350 A | 8/1976 | Hudgin et al. |
| 4,020,216 A | 4/1977 | Miller |
| 4,055,682 A | 10/1977 | Merrill |
| 4,078,015 A | 3/1978 | Leitheiser |
| 4,100,309 A | 7/1978 | Micklus |
| 4,116,898 A | 9/1978 | Dudley |
| 4,118,485 A | 10/1978 | Eriksson |
| 4,119,094 A | 10/1978 | Micklus |
| 4,143,423 A | 3/1979 | Sternlieb |
| 4,145,513 A | 3/1979 | Dalibor |
| 4,156,067 A | 5/1979 | Gould |
| 4,175,161 A | 11/1979 | Fogle |
| 4,267,295 A | 5/1981 | Gallop et al. |
| 4,298,002 A | 11/1981 | Ronel |
| 4,318,947 A | 3/1982 | Joung |
| 4,326,532 A | 4/1982 | Hammar |
| 4,349,467 A | 9/1982 | Williams et al. |
| 4,369,229 A | 1/1983 | Shah |
| 4,373,009 A | 2/1983 | Winn |
| 4,405,773 A | 9/1983 | Loshaek |
| 4,417,892 A | 11/1983 | Meisch |
| 4,430,458 A | 2/1984 | Tighe |
| 4,434,797 A | 3/1984 | Silander |
| 4,459,317 A | 7/1984 | Lambert |
| 4,459,318 A | 7/1984 | Hyans |
| 4,487,808 A | 12/1984 | Lambert |
| 4,515,593 A | 5/1985 | Norton |
| 4,516,970 A | 5/1985 | Kaufman |
| 4,529,614 A | 7/1985 | Burns |
| 4,535,006 A | 8/1985 | Naunapper et al. |
| 4,585,666 A | 4/1986 | Lambert |
| 4,589,873 A | 5/1986 | Schwartz |
| RE32,307 E | 12/1986 | Glatt et al. |
| 4,636,195 A | 1/1987 | Wolinsky |
| 4,642,267 A | 2/1987 | Creasy |
| 4,666,437 A | 5/1987 | Lambert |
| 4,670,313 A | 6/1987 | Saudagar |
| 4,678,671 A | 7/1987 | Feijen |
| 4,690,684 A | 9/1987 | McGreevy et al. |
| 4,690,844 A | 9/1987 | Saudagar |
| 4,729,914 A | 3/1988 | Kliment |
| 4,740,207 A | 4/1988 | Kreamer |
| 4,753,652 A | 6/1988 | Langer et al. |
| 4,755,379 A | 7/1988 | Jozefonvicz |
| 4,758,151 A | 7/1988 | Arru et al. |
| 4,768,507 A | 9/1988 | Fischell et al. |
| 4,776,337 A | 10/1988 | Palmaz |
| 4,795,458 A | 1/1989 | Regan |
| 4,824,436 A | 4/1989 | Wolinsky |
| 4,832,688 A | 5/1989 | Sagae et al. |
| 4,838,876 A | 6/1989 | Wong |
| 4,888,009 A | 12/1989 | Lederman et al. |
| 4,922,905 A | 5/1990 | Strecker |
| 4,950,227 A | 8/1990 | Savin et al. |
| 5,007,926 A | 4/1991 | Derbyshire |
| 5,019,090 A | 5/1991 | Pinchuk |
| 5,041,100 A | 8/1991 | Rowland et al. |
| 5,053,048 A | 10/1991 | Pinchuk |
| 5,059,211 A | 10/1991 | Stack et al. |
| 5,087,244 A | 2/1992 | Wolinsky et al. |
| 5,091,205 A | 2/1992 | Fan |
| 5,092,877 A | 3/1992 | Pinchuk |
| 5,102,417 A | 4/1992 | Palmaz |
| 5,108,416 A | 4/1992 | Ryan et al. |
| 5,135,484 A | 8/1992 | Wright |
| 5,158,548 A | 10/1992 | Lau et al. |
| 5,171,217 A | 12/1992 | March et al. |
| 5,171,812 A | 12/1992 | Domb |
| 5,175,235 A | 12/1992 | Domb et al. |
| 5,192,307 A | 3/1993 | Wall |
| 5,221,698 A | 6/1993 | Amidon et al. |
| 5,226,913 A | 7/1993 | Pinchuk |
| 5,234,456 A | 8/1993 | Silvestrini |
| 5,234,457 A | 8/1993 | Anderson |
| 5,236,503 A | 8/1993 | Jones |
| 5,240,963 A | 8/1993 | Domb et al. |
| 5,242,399 A | 9/1993 | Lau et al. |
| 5,272,012 A | 12/1993 | Opolski |
| 5,281,200 A | 1/1994 | Corso, Jr. et al. |
| 5,282,823 A | 2/1994 | Schwartz et al. |
| 5,304,121 A | 4/1994 | Sahatjian |
| 5,328,470 A | 7/1994 | Nabel et al. |
| 5,330,467 A | 7/1994 | Abela |
| 5,334,142 A | 8/1994 | Paradis |
| 5,334,201 A | 8/1994 | Cowan |
| 5,336,178 A | 8/1994 | Kaplan et al. |
| 5,336,615 A | 8/1994 | Bell et al. |
| 5,342,348 A | 8/1994 | Kaplan |
| 5,342,621 A | 8/1994 | Eury |
| 5,345,933 A | 9/1994 | Peterson et al. |
| 5,370,614 A | 12/1994 | Amundson et al. |
| 5,380,299 A | 1/1995 | Fearnot et al. |
| 5,383,928 A | 1/1995 | Scott et al. |
| 5,385,548 A | 1/1995 | Williams et al. |
| 5,419,760 A | 5/1995 | Narcisco, Jr. |
| 5,423,885 A | 6/1995 | Williams |
| 5,429,634 A | 7/1995 | Narcisco |
| 5,437,889 A | 8/1995 | Jones |
| 5,439,446 A | 8/1995 | Barry |
| 5,439,686 A | 8/1995 | Desai et al. |
| 5,443,458 A | 8/1995 | Eury |
| 5,443,496 A | 8/1995 | Schwartz et al. |
| 5,447,724 A | 9/1995 | Helmus et al. |
| 5,457,113 A | 10/1995 | Cullinan et al. |
| 5,462,937 A | 10/1995 | Cullinan et al. |
| 5,464,450 A | 11/1995 | Buscemi et al. |
| 5,464,650 A | 11/1995 | Berg et al. |
| 5,475,052 A | 12/1995 | Rhee et al. |
| 5,486,191 A | 1/1996 | Pasricha et al. |
| 5,500,013 A | 3/1996 | Buscemi et al. |
| 5,512,055 A | 4/1996 | Domb et al. |
| 5,516,781 A | 5/1996 | Morris et al. |
| 5,527,337 A | 6/1996 | Stack et al. |
| 5,545,208 A | 8/1996 | Wolff et al. |
| 5,545,213 A | 8/1996 | Keogh et al. |
| 5,551,954 A | 9/1996 | Buscemi et al. |
| 5,554,182 A | 9/1996 | Dinh et al. |
| 5,562,922 A | 10/1996 | Lambert |
| 5,571,166 A | 11/1996 | Dinh et al. |
| 5,575,815 A | 11/1996 | Slepian et al. |
| 5,578,075 A | 11/1996 | Dayton |
| 5,588,962 A | 12/1996 | Nicholas et al. |
| 5,591,227 A | 1/1997 | Dinh et al. |
| 5,599,352 A | 2/1997 | Dinh et al. |
| 5,603,694 A | 2/1997 | Brown et al. |
| 5,605,696 A | 2/1997 | Eury et al. |
| 5,607,417 A | 3/1997 | Batich et al. |

| | | | | | | |
|---|---|---|---|---|---|---|
| 5,607,475 | A | 3/1997 | Cahalan et al. | WO | 7900638 | 9/1979 |
| 5,609,629 | A | 3/1997 | Fearnot et al. | WO | 8603127 | 4/1986 |
| 5,624,411 | A | 4/1997 | Tuch | WO | 8706007 | 3/1987 |
| 5,653,760 | A | 8/1997 | Saffran | WO | 8707156 | 10/1987 |
| 5,679,400 | A | 10/1997 | Tuch | WO | WO 9112779 | 9/1991 |
| 5,776,184 | A | 7/1998 | Tuch | WO | WO 9215286 | 9/1992 |
| 5,824,048 | A | 10/1998 | Tuch | WO | WO 9013332 | 12/1992 |
| 5,824,049 | A | 10/1998 | Ragheb et al. | WO | WO 00/45744 | 8/2000 |
| 5,833,651 | A | 11/1998 | Donovan et al. | WO | WO 01/91918 | 12/2001 |
| 5,837,008 | A | 11/1998 | Berg et al. | | | |
| 5,843,172 | A | 12/1998 | Yan | | | |
| 5,851,217 | A | 12/1998 | Wolff et al. | | | |
| 5,851,231 | A | 12/1998 | Wolff et al. | | | |
| 5,871,535 | A | 2/1999 | Wolff et al. | | | |
| 5,873,904 | A | 2/1999 | Ragheb et al. | | | |
| 5,879,697 | A | 3/1999 | Ding et al. | | | |
| 5,900,246 | A | 5/1999 | Lambert | | | |
| 5,981,568 | A | 11/1999 | Kunz et al. | | | |
| 5,997,468 | A | 12/1999 | Wolff et al. | | | |
| 6,096,070 | A | 8/2000 | Ragheb et al. | | | |
| 6,099,561 | A | 8/2000 | Alt | | | |
| 6,099,562 | A | 8/2000 | Ding et al. | | | |
| 6,120,536 | A | 9/2000 | Ding et al. | | | |
| 6,120,847 | A | 9/2000 | Yang et al. | | | |
| 6,146,358 | A | 11/2000 | Rowe | | | |
| 6,153,252 | A | 11/2000 | Hossainy et al. | | | |
| 6,187,370 | B1 | 2/2001 | Dinh et al. | | | |
| 6,206,915 | B1 | 3/2001 | Fagan et al. | | | |
| 6,206,916 | B1 | 3/2001 | Furst | | | |
| 6,228,845 | B1 | 5/2001 | Donovan et al. | | | |
| 6,273,913 | B1 | 8/2001 | Wright et al. | | | |
| 6,299,604 | B1 | 10/2001 | Ragheb et al. | | | |
| 6,355,055 | B1 | 3/2002 | Wasksman et al. | | | |
| 6,379,382 | B1 | 4/2002 | Yang | | | |
| 6,379,691 | B1 | 4/2002 | Tedeschi et al. | | | |
| 6,395,326 | B1 | 5/2002 | Castro et al. | | | |
| 6,406,754 | B2 | 6/2002 | Chappa et al. | | | |
| 7,056,550 | B2 * | 6/2006 | Davila et al. ............... 427/2.24 | | | |
| 7,208,010 | B2 * | 4/2007 | Shanley et al. ............ 623/1.42 | | | |
| 2002/0051730 | A1 | 5/2002 | Bodnar et al. | | | |
| 2002/0098278 | A1 | 7/2002 | Bates et al. | | | |

FOREIGN PATENT DOCUMENTS

| | | |
|---|---|---|
| DE | 2321086 | 11/1974 |
| EP | 0014238 | 11/1979 |
| EP | 0093093 | 11/1983 |
| EP | 0093094 | 11/1983 |
| EP | 149693 | 1/1985 |
| EP | 166998 | 1/1986 |
| EP | 0217771 | 4/1987 |
| EP | 470246 B1 | 9/1991 |
| EP | 747069 A2 | 12/1996 |
| EP | 627226 B1 | 12/1998 |
| FI | 73701 | 6/1987 |
| GB | 1600963 | 10/1981 |
| GB | 2128500 | 5/1984 |
| GB | 2122510 | 6/1984 |
| GB | 2163436 | 2/1986 |
| GB | 2190387 | 8/1986 |
| JP | 49008583 | 6/1944 |
| JP | 51000194 | 11/1948 |
| JP | 55035650 | 6/1950 |
| JP | 57031868 | 12/1953 |
| JP | 57119756 | 12/1953 |
| JP | 58105759 | 7/1954 |
| JP | 58206753 | 8/1954 |
| JP | 57014358 | 11/1958 |
| JP | 61168365 | 2/1959 |
| JP | 503507 | 5/1973 |
| JP | 49-132219 | 12/1973 |
| JP | 7503507 | 11/1975 |
| JP | 480555946 | 10/1987 |

OTHER PUBLICATIONS

Amplatz, "A New Simple Test for Thrombogenicity", *Radiology*, 120: 53-55, Jul. 1976.

Amplatz, "A Simple Non-Thrombogenic Coating", *Investigative Radiology*, vol. 6, Jul.-Aug. 1971, p. 280.

Anderson, "A Scanning Electron Microscope Study of Angiographic Catheters and Guidewires", *Radiology*, 111: 567-571, Jun. 1974.

Anderson, "Anticoagulation Techniques for Angiography", *Radiology*, 111: 573-576, Jun. 1974.

Cramer, "A Preliminary Human Study with a Simple Non-Thrombogenic Catheter", *Radiology*, vol. 100, Jul.-Sep. 1971, p. 421.

Cramer, "Reduction of the Surgical Complication Rate by the Use of a Hypothrombogenic Catheter Coating", *Diagnostic Radiology*, vol. 109, Oct.-Dec. 1973, p. 585.

Deutsch et al., "Low Stress Angioplasty at 60° C.: Attenuated Arterial Barotrauma", *Circuration* (Supp. III) 82:0281 (abstract) (Oct. 1990).

Durst, "Flow Cell Evaluation of Nonthrombogenic Materials", *Radiology*, 106: 507-511, Mar. 1973.

Esquivel, "Reduced Thrombogenic Characteristics of Expanded Polytetrafluoroethylene and Polyurethance Arterial Graphs After Heparin Bonding", *Surgery*, vol. 95, Jan. 1984, p. 102.

Frech, R.S. et al., "A Simple Noninvasive Technique to Test Nonthrombogenic Surfaces", Am. J. Roentgenol., Radium Ther. & Nucl. Med. 113(4):765-768 (1971).

Haut, "Complication Rates of Transfemoral and Trans-aortic Catheterization", *Surgery*, vol. 63, No. 4, Apr. 1968, p. 594.

Horbit, "Absorption of Proteins from Plasma to a Series of Hydrophillic-Hydrophobic Copolymers I Analysis with the In Situ Radioiodination Technique", *J. of Biomedical Materials Research*, vol. 15, p. 403 (1981).

Klarscov, "Catheter-Associated Bacteriuria", *Acta. Obstet. GynecoL Scanned* 65:295-299, 1986.

Linhardt, "Differential Anticoagulant Activity of Heparin Fragments Prepared Using Microbial Heparinase", *J. Biological Chemistry*, vol. 257, No. 13, Jul. 1982, p. 7310.

Lipton, "Evaluation of Catheter Thrombogenicity In Vivo with Indium Labelled Platelets", *Radiology*, 135:191-194, Apr. 1980.

McCarty, "Thrombogenicity of Guidewires", *The American Journal of Cardiology*, vol. 32, Dec. 1973, p. 943.

Miyam et al., "A New Antithrombogenic Heparinized Polymer", *J. Bio Med Mater. Res.*, vol. 11, p. 251, 1977.

Mori et al., "The Effect of Released Heparin from the Heparinized Hydrophilic Polymer (HRSD) on the Process of Thrombus Formation", Trans. Am. Soc. Artif. Intern. Organs, vol. XXIV, p. 736, 1978.

Nichols, "Effect of Heparin Bonding on Catheter Induced Fibrin Formation and Platelet Activation", *Circulation*, 70, No. 5, 843-850, 1984.

Nishi, "Complex-Forming Poly(Oxyethylene) Poly (acrylic acid) Interpenetrating Polymer Networks, I. Preparation, Structure and Physco Elastic Properties", *Macromolecules*, vol. 18, No. 8, 1985, p. 1519.

Noishiki et al., "Prevention of Thrombosis-Related Complications in Cardiac Catheterization and Angiography Using Heparinized Catheter, (Anthron)", *ASAIO*, vol. 10(3), Jul.-Sep. 1987, p. 359.

Okano, "Effect of Hydrophilic and Hydrophobic Microdomains on Mode of Interaction Between Block Polymer and Blood Platelets", *Journal of Biomedical Materials Research*, vol. 15, p. 393, 1981.

Ovitt, "Guidewire Thrombogenicity and its Reduction". Radiology, 111: 43-46, Apr. 1974.

Ramsay, "An Experimental Study of Hydrophilic Plastics for Urological Use", *British Journal of Urology*, 1986, 58, p. 70.

Roberts, "Thrombogenicity of Arterial Catheters and Guidewires," *British Journal of Radiology*, vol. 50, p. 415, 1977.

Shook, "Everting (toposcopic) Catheter for Broad Clinical Application", *Transactions of the ASME*, vol. 108, May 1986, p. 168.

Takayasu, "Plastic-Coated Guidewire for Hepatic Arteriography," *Radiology*, vol. 66, No. 2, p. 545.

Theodore, A.N. et al., "A Convenient Preparation of Acrylic-Urethane Nonaqueous Dispersions", Journal of Coatings Technology, 57(721):67-71 (1985).

* cited by examiner

STENT LINING

CROSS REFERENCE TO RELATED APPLICATIONS

This application is a continuation of application Ser. No. 10/059,420, filed Jan. 31, 2002 now U.S. Pat. No. 6,890,339, which is a continuation of application Ser. No. 09/129,280, filed Aug. 5, 1998, issued as U.S. Pat. No. 6,364,893 B1, which is a continuation of application U.S. Ser. No. 08/717,290, filed Sep. 20, 1996, issued as U.S. Pat. No. 5,843,089, which is a continuation-in-part of application of Ser. No. 08/507,844 filed Jul. 27, 1995, issued as U.S. Pat. No. 5,685,847 which is a continuation-in-part of Ser. No. 08/268,999, filed Jun. 30, 1994, issued as U.S. Pat. No. 5,439,446. U.S. Ser. No. 08/717,290, filed Sep. 20, 1996, issued as U.S. Pat. No. 5,843,089, is also a continuation-in-part of Ser. No. 08/097,248 filed Jul. 23, 1993, issued as U.S. Pat. No. 5,674,192, which is a continuation-in-part of Ser. No. 07/795,976 filed Nov. 22, 1991, issued as U.S. Pat. No. 5,304,121 which is a continuation-in-part of Ser. No. 07/635,732 filed Dec. 28, 1990, now abandoned which is a continuation-in-part of Ser. No. 07/451,507 filed Dec. 15, 1989 issued as U.S. Pat. No. 5,135,516. The entire contents of each of these applications is hereby incorporated by reference.

BACKGROUND OF THE INVENTION

The invention relates to the lining of bodily stents.

Angioplasty, which involves the insertion of a catheter, e.g., a balloon catheter, into a blood vessel to expand an occluded region of the blood vessel, is frequently used to treat arteriosclerosis. Restenosis, or closing of the vessel, is a process that may occur following angioplasty. This process may be characterized by the proliferation of smooth muscle cells stimulated by the angioplasty treatment. Restenosis may also occur as a result of clot formation following angioplasty, due to injury to the vessel wall which triggers the natural clot-forming cascade of the blood.

A number of different approaches have been taken to prevent post-angioplasty vessel reclosure. One such approach has been the placement of a medical prosthesis, e.g., an intravascular metal stent, to mechanically keep the lumen open. For example, an intravascular stent made of an expandable stainless steel wire mesh tube has been used to prevent post angioplasty restenosis and vessel reclosure. The stent may be formed of wire configured into a tube and is usually delivered into the body lumen using a catheter. The catheter carries the prosthesis in a reduced-size form to the desired site. When the desired location is reached, the prothesis is released from the catheter and expanded so that it engages the lumen wall. Stents are typically fabricated from metals, alloys, or plastics and remain in the blood vessel indefinitely.

SUMMARY OF THE INVENTION

The invention features a catheter assembly for delivering a stent to a body lumen and lining the stent with a hydrogel to reduce shear forces and flow disturbances in the blood, protect damaged cells adjacent to the stent, reduce platelet deposition at the stent site, and/or deliver a drug to reduce or prevent restenosis of stented lumens. The assembly includes a catheter which has a balloon at least a portion of which is coated with a hydrogel. The assembly also includes an expansible stent mounted on the balloon in a contracted condition for passage with the catheter to a site of a body lumen. Expansion of the balloon lodges the stent in the body lumen with the hydrogel deposited on an inner surface of the stent as a lining. The hydrogel may be crosslinked to form a relatively permanent lining on the inner surfaces of the stent or left uncrosslinked to form a relatively degradable lining on the inner surfaces of the stent. Preferably, the longevity of a crosslinked form of a given hydrogel as a stent lining is at least twice that of its uncrosslinked form.

The hydrogel is selected from the group consisting of a polyacid, e.g., a poly(acrylic acid) or a polycarboxylic acid, cellulosic polymer, collagen, gelatin, albumin, alginate, poly 2-hydroxy ethyl methyl acrylate (HEMA), polyvinylpyrrolidone, maleic anhydride polymer, polyamide, polyacrylamide, polyvinyl alcohol, polyethylene glycol, polyethylene oxide, and polysaccharide, e.g., a mucopolysaccharide such as hyaluronic acid. For example, the hydrogel may be a poly(acrylic acid), e.g., CARBOPOL® 941 poly (acrylic acid) (BF Goodrich), in a crosslinked or uncrosslinked form.

In some cases, the hydrogel may be crosslinked prior to lining the stent. For example, the hydrogel coating on a balloon may be contacted with a primer dip before the hydrogel is deposited onto the inner surfaces of a stent. Alternatively, the hydrogel lining may be contacted with a crosslinking agent in situ, i.e., the balloon portion of the catheter with a coating of uncrosslinked hydrogel is inserted into the body and after the deployment of the stent in the body lumen and deposition of the hydrogel onto the inner surfaces of the stent, the hydrogel is contacted with a crosslinking agent.

The hydrogel may include a therapeutic agent, e.g., a drug, to reduce or prevent clotting and/or restenosis at the stent site. For example, the therapeutic agent may reduce or eliminate acute thrombosis of the stent and reduce in-stent restenosis or interfere with cell metabolism (e.g., an anti-metabolite), thereby killing undesired cells. The therapeutic agent may be an anti-platelet drug, anticoagulant drug, anti-metabolite drug, anti-angiogenic drug, or anti-proliferative drug. The therapeutic agent may be an anti-thrombogenic agent such as heparin, PPACK, enoxaprin, aspirin, and hirudin or a thrombolytic agent such as urokinase, streptokinase, and tissue plasminogen activator. The hydrogel may also include an agent which inhibits platelet deposition or smooth muscle cell proliferation. The agent may also be a nucleic acid which encodes a therapeutic protein, e.g., a naked nucleic acid or a nucleic acid incorporated into a viral vector or liposome. By naked nucleic acid is meant an uncoated single or double stranded DNA or RNA molecule not incorporated into a virus or liposome. Antisense oligonucleotides which specifically bind to complementary mRNA molecules and thereby reduce or inhibit protein expression can also be delivered to the stent site via the hydrogel coating on the balloon catheter. The drug may be incorporated into microspheres to prolong the time over which a delivered drug is released and minimize spreading of the delivered drug to non-target sites.

Rather than administering the hydrogel lining via a coating on a balloon, the catheter may include a delivery port for administering a hydrogel to the inner surfaces of the stent. For example, the balloon may include a first layer and a second outer apertured layer overlaying the delivery port. The hydrogel is administered through the outer apertured layer of the balloon to contact the inner surfaces of the stent to create a lining therein. After the hydrogel is applied to the stent, a crosslinking agent may be administered to contact the hydrogel. For example, an alginate hydrogel can be crosslinked by contacting it with calcium gluconate, and a hyaluronic acid hydrogel can be crosslinked by contacting it with divinyl glycol.

Lining a stent using a porous balloon, e.g., a channeled balloon, is accomplished by deploying the stent positioned over the porous balloon and then infusing a hydrogel through the pores in the balloon to line the inner surfaces of the stent with a polymeric layer to facilitate smooth flow of blood through the stent. The hydrogel fills the interstices of a mesh stent creating a smooth lining inside the stent.

Alternatively, one or more delivery ports may be located proximal to the balloon over which the stent is mounted, i.e., upstream of the stent with respect to the blood flow, and the hydrogel administered via the delivery port and carried to the inner surfaces of the stent by the blood flow.

The invention also features a method for lining a stent which includes the steps of providing a catheter assembly including a balloon at least a portion of which is coated with a hydrogel over which is mounted an expansible stent in a contracted condition, introducing the assembly into a body lumen, and inflating the balloon to lodge the stent in the body lumen and to release the hydrogel from the coated portion of the balloon to the inner surfaces of the stent to create a lining. Preferably, the body lumen is a blood vessel, more preferably it is an artery, such as an artery occluded by an arteriosclerotic plaque.

Also within the invention is a method of lining a stent which has been previously deployed in a body lumen of a patient. The method includes the steps of providing a catheter including a balloon at least a portion of which is coated with a hydrogel, introducing the catheter into the body lumen, advancing the catheter in the body lumen until the balloon is positioned proximate to the inner surfaces of the stent, and inflating the balloon to release the hydrogel from the coated portion of the balloon to the inner surfaces of the stent to create a lining. The catheter may include a sheath over the hydrogel-coated portion of the balloon which is removed prior to inflating the balloon.

A previously-deployed stent may also be lined using a catheter which includes a balloon and delivery port, the balloon portion of which contains a first layer and a second outer aperatured layer overlying the delivery port. The method includes the steps of introducing the catheter into the body lumen, advancing the catheter in the body lumen until the outer aperatured layer is positioned proximate to the inner surfaces of the stent, delivering a hydrogel into a space between the first layer and the second outer aperatured layer, and inflating the balloon to press the hydrogel through the outer aperatured layer thereby depositing the hydrogel on the inner surfaces of the stent as a lining.

A previously-deployed permeable stent, e.g., an open mesh metal stent, in the region of a blood vessel affected by an aneurism may be selectively lined with a hydrogel to render the portion of the stent proximate to the aneurism impermeable, thereby preventing blood flow into the aneurism. By "selectively lining" is meant depositing a lining material, e.g., a hydrogel, in a desired region of the inner surface of a stent while leaving other regions of the inner surface of the stent free from the lining material. The hydrogel lining is delivered to the stent as a coating on a balloon portion of a catheter or via ports of a channeled balloon. For example, a method of selectively lining a permeable stent to treat an aneurism, includes the steps of providing a balloon catheter with at least a portion of the balloon coated with a hydrogel; introducing the catheter into an aneurismal blood vessel in which a permeable stent has previously been deployed in the region of the aneurism; advancing the catheter in the affected vessel until the coated portion is positioned proximate to the aneurism; and inflating the balloon to release the hydrogel from the coated portion to an inner surface of the stent proximate to the aneurism. The hydrogel lining renders the inner surface of the stent near the aneurism impermeable, thereby reducing or preventing blood flow into the aneurism, but permitting blood flow through the unlined portions of the stent to or from branching blood vessels in an area of the vessel unaffected by the aneurism.

Other features and advantages of the invention will be apparent from the following description of the preferred embodiments thereof, and from the claims.

DETAILED DESCRIPTION

Figure 1:
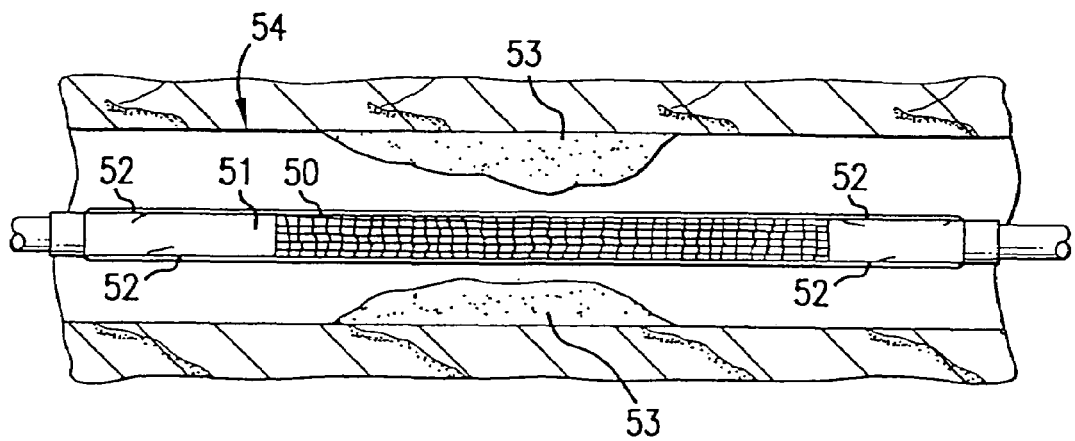
FIG. 1 is a cross-sectional view of a hydrogel-coated balloon catheter with a stent mounted on the balloon portion of a catheter in the region of a thrombus before radial expansion of the balloon section and stent.

The inner surfaces of a stent may be lined with a hydrogel post-deployment or simultaneously with deployment of the stent into a body lumen. The hydrogel is delivered as a coating on a balloon dilatation catheter. The hydrogel is released from the balloon onto the stent by expanding the balloon into the stent forcing the hydrogel onto the inner surface of the stent.

The hydrogel which has been deposited onto the stent provides a smooth surface lining to protect cells of the lumen, e.g., a blood vessel wall, which may have been damaged during deployment of the stent, e.g., when the stent is lodged into the vessel wall. The stent lining also reduces flow disturbances, e.g., turbulence, and shear in the bloodstream in the area of a blood vessel in which the stent is lodged. The stent lining may also reduce or prevent blood flow through a particular lined region of a stent, e.g., in the region of an aneurism.

Stents may be lined with a hydrogel in the absence of drug or in the presence of drug. In addition to the mechanical advantages described above, the addition of drugs into the hydrogel provides further therapeutic benefits. For example, a hydrogel lining which contains albumin reduces platelet deposition at the stent site. Other drugs, e.g., agents which reduce the proliferation of smooth muscle cells, can also be incorporated into the hydrogel stent lining to reduce intimal smooth muscle cell proliferation which may contribute to restenosis at the stent site. The stent lining may also be used to deliver a drug, e.g., heparin, to enhance antithrombogenicity.

Preparation of a Hydrogel-Coated Angioplasty Balloon

A hydrogel coating on an angioplasty balloon was formed as follows. The surface of the balloon (polyethylene) of an angioplasty catheter was prepared by wiping down the catheter with clean cloth. The balloon typically has an outer diameter (O.D) of about 3.5 mm (inflated). The balloon was dipped in a 10% solution of CARBOPOL® 941 poly(acrylic acid) having a molecular weight of about 1,200,000 Daltons in dimethylformamide (DMF) and tertiarybutyl alcohol. After drying at about 85° C. for 30 minutes, a smooth coating was obtained. The balloon was then oven-dried for 8 hours at 50° C.

Alternatively, the poly(acrylic acid) coating may be crosslinked by dipping the poly(acrylic acid)-coated balloon into a primer dip of 4,4' diphenylmethane diisocyanate (MDI) in methylketone for 30 min. and drying in an air oven at 85° C. for 30 min.

One function of the drying steps is to remove solvent from the coating. The surface of the balloon becomes instantly lubricious upon exposure to water. The poly(acrylic acid) is typically at a concentration of about 0.1 to 50% by weight. The formation of the hydrogel is further described in U.S. Pat. No. 5,091,205, hereby incorporated by reference.

Other hydrogel polymers, such as collagen, albumin, derivatized albumin, gelatin, polyvinyl alcohol (PVA), cellulosics, alginates, acrylics, HEMA, polyethylene glycols, polyethylene oxides, polyacids, polyanhydrides, and polyacrylamides can be used to coat the balloon. Like the poly(acrylic acid) polymer coating, these hydrogel polymers are released from the balloon onto the inner surfaces of a stent by compression of the coated balloon against the stent. The hydrogel polymers used are swellable but not dissolvable. As a result, a sheath over the hydrogel-coated balloon is not required to prevent loss of the hydrogel coating prior to release onto the inner surface of the stent. However, a sheath may be used in any of the embodiments discussed herein to facilitate placement of the catheter and/or deployment of the catheter or stent. For simultaneous stent deployment and lining, an expansible stent in a contracted form is placed over the hydrogel-coated balloon portion of the catheter prior to introduction of the catheter/stent assembly into the body. A drug such as an anti-thrombogenic agent may be applied to the coating or incorporated into the coating. For example, a solution of 10,000 units sodium heparin (Fisher Scientific, Pittsburgh, Pa.; USP Grade; 1000 units/ml which is then added to 650 cc distilled water) may be applied to the hydrogel coating by dipping the coated catheter into the heparin solution for about 1 minute at room temperature.

The heparin does not form a complex with the hydrogel solution and is therefore freely released in response to compression of the hydrogel. A drug may be formulated to be rapidly released upon compression of the hydrogel, e.g., upon release of the hydrogel from the balloon to the inner surfaces of the stent, or to be slowly released over time, e.g., by diffusion from the hydrogel stent lining. Alternatively, the drug, e.g., urokinase, may form a complex with the hydrogel, or the drug releasing system may be the hydrogel itself, e.g., nitrosylated albumin which releases nitric oxide.

After a catheter is prepared for use as discussed above, the catheter may be introduced into the patient using known methods. The balloon is then expanded at a desired location to deploy the stent and simultaneously release the hydrogel from the balloon to line the stent. The hydrogel is deposited and remains on the stent as a lining after the balloon is deflated. The hydrogel coating can also be applied to a pre-existing stent, e.g., one that has already been expanded and/or deployed in a body lumen, of a patient. Lining a previously-deployed stent is accomplished by introducing the hydrogel-coated balloon catheter into the vessel, positioning the balloon portion adjacent to the previously-deployed stent, and inflating the balloon portion against the inner surfaces of the previously-deployed expanded stent to release the hydrogel thereby lining the stent.

EXAMPLE 1

Figure 2:
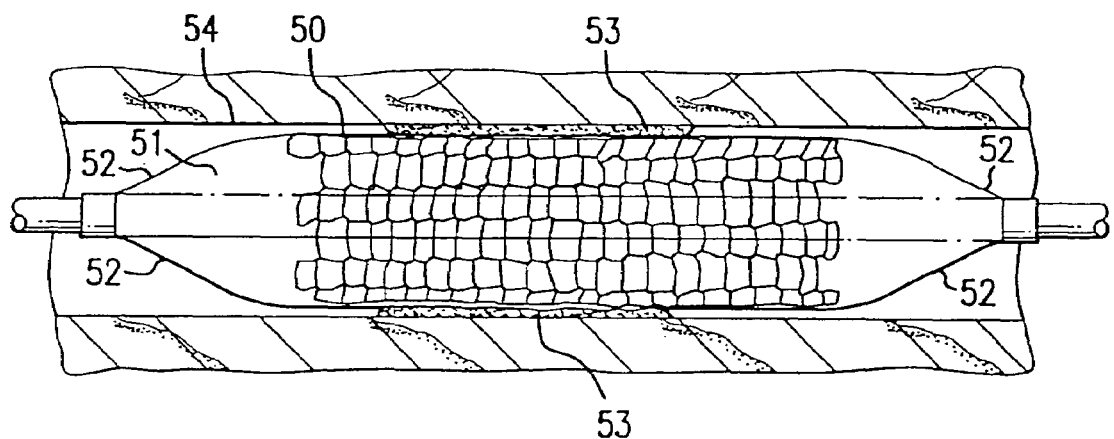
FIG. 2 is a cross-sectional view of a stent compressed against a wall of a body lumen by radial expansion of the balloon portion of the catheter and release of the hydrogel from the balloon portion of the catheter onto the inner surfaces of the stent.
Figure 3:
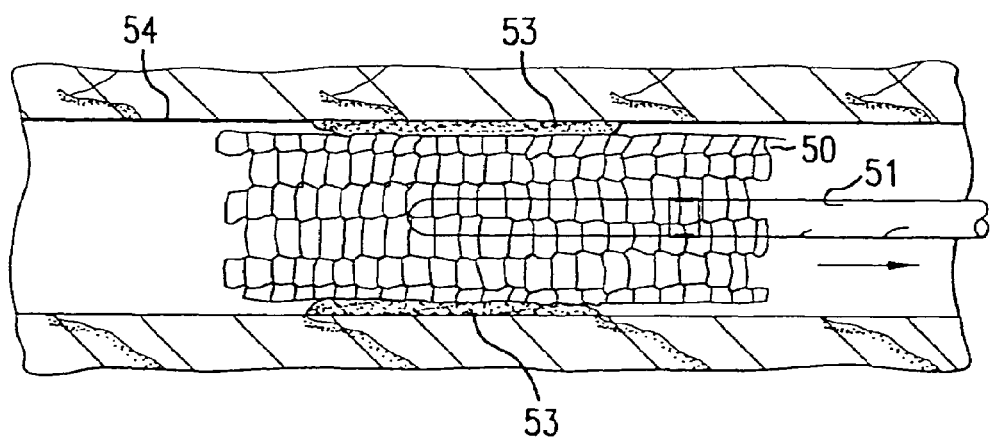
FIG. 3 is a cross-sectional view of a hydrogel-lined stent positioned inside the compressed thrombus as the catheter is removed.

Lining of an Intravascular Stent with a Hydrogel Simultaneously with Deployment of the Stent into a Body As shown in FIG. 1, a stent 50 is placed over the balloon catheter 51 which is coated with a hydrogel coating 52 in the presence or absence of a drug. The balloon 51 and stent 50 are advanced until they reach the region of the occlusion 53 in the vessel 54. After the balloon 51 and the stent 50 have been positioned inside the vessel 54, the stent 50 is radially expanded and the hydrogel coating 52 released from the balloon 51 onto an inner surface of the stent 50 by the admission of pressure to the balloon 51. As a result, the stent is compressed against the vessel wall 54 with the result that occlusion 53 is compressed, and the vessel wall 54 surrounding it undergoes a radial expansion. The pressure from inflating the balloon also releases the hydrogel coating 52 onto the inner surface of the stent 50, thus lining it. The stent 50 is held in position in the expanded state as shown in FIG. 2. The pressure is then released from the balloon and the catheter is withdrawn from the vessel, leaving the hydrogel as a lining of the deployed stent, as shown in FIG. 3.

In the embodiments in which the hydrogel stent lining contains a drug, the hydrogel and drug may be selected such that an initial high dosage is delivered to adjacent tissue upon initial compression of the hydrogel followed by a slow, sustained time-release of drug remaining in the hydrogel lining. Preferred hydrogel-drug combinations are those that employ a binding of the drug, such as electrostatic binding, e.g., by using a poly(acrylic acid) hydrogel in combination with an ammonium cation and heparin or urokinase. In this case, the coating continues to release drug after expansion of the stent and removal the balloon catheter. The stent may be a balloon-expansible stent as described above or a self-expanding stent, e.g., of the type formed with superelastic materials such as Nitinol.

EXAMPLE 2

Figure 4:
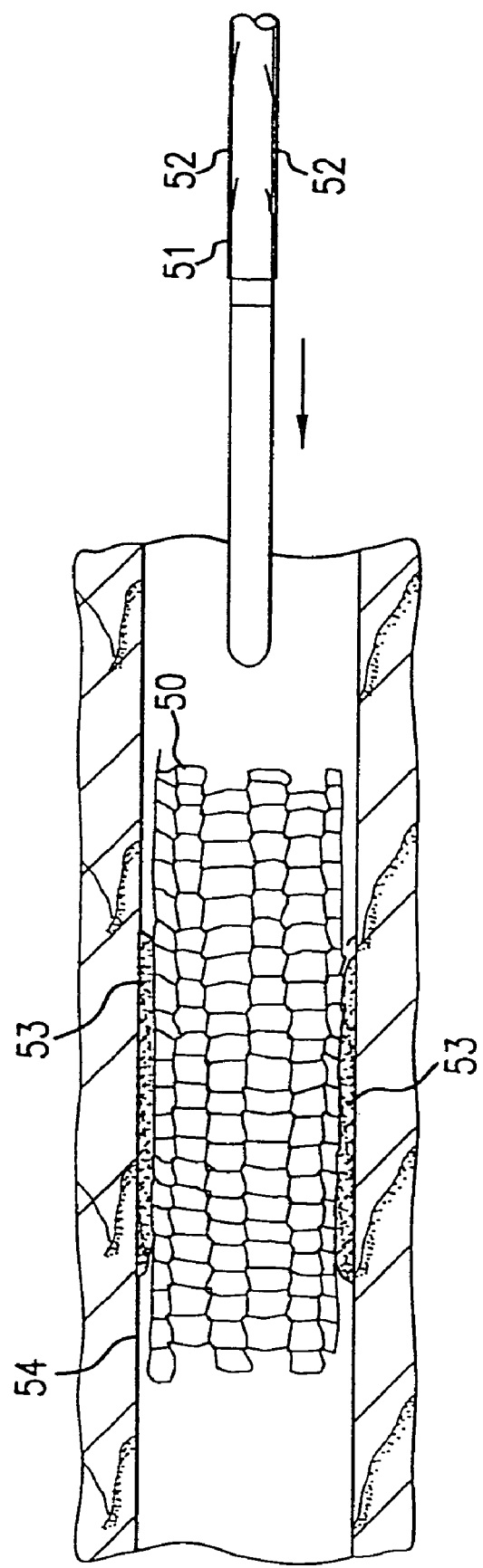
FIG. 4 is a cross-sectional view of a stent previously-deployed in a body lumen and a hydrogel-coated catheter prior to expansion of the balloon portion to release the hydrogel onto the inner surfaces of the previously-deployed stent.

Lining of an Intravascular Stent With a Hydrogel Poat-Deployment of the Stent Into a Body A stent 50 that has been previously been deployed, i.e., expanded and lodged in the vessel 54, may be lined by introducing a balloon catheter 51 with a hydrogel coating 52 into the body lumen any time after stent deployment as shown in FIG. 4. The balloon portion of the catheter is positioned such that the hydrogel-coated portion is proximate to the inner surfaces of the stent, and the balloon is inflated so that the hydrogel coating of the balloon contacts the inner surface of the stent and compresses the hydrogel against the stent thereby releasing the hydrogel from the balloon to the stent creating a lining therein. Alternatively, an infusion balloon or channel balloon may be used to administer a hydrogel lining to a previously-deployed stent as described below.

Figure 5:
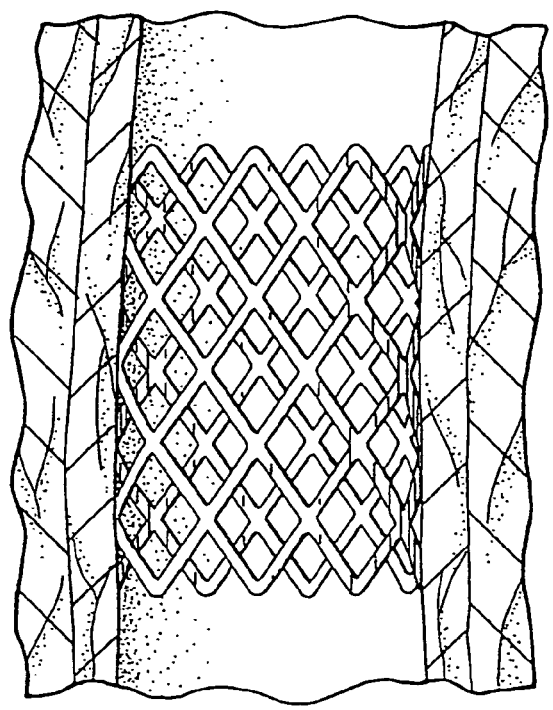
FIG. 5 is a photograph of a model body lumen in which an open mesh metal stent has been deployed.
Figure 6:
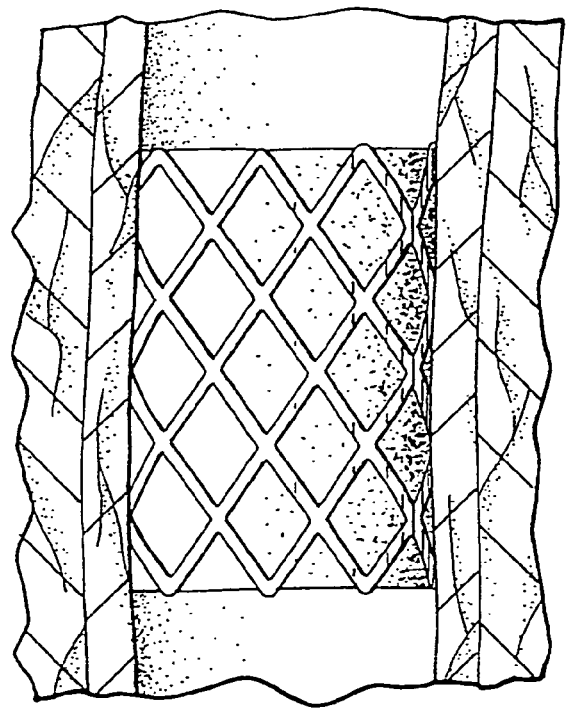
FIG. 6 is a photograph of a model body lumen in which a previously-deployed open mesh metal stent has been lined with a hydrogel using a hydrogel-coated balloon catheter.

A Palmaz-Schatz stent was expanded in a model blood vessel, e.g., tygon tubing, as shown in FIG. 5. A polyethylene angioplasty balloon catheter was coated with a hydrogel (approximately 10% solution of poly(acrylic acid); e.g., 10-20% poly(acrylic acid)). To line the previously-deployed Palmaz-Schatz stent, the catheter was inserted into the model blood vessel and advanced to the area of the expanded stent, positioning the balloon portion proximate to the inner surfaces of the stent. The balloon was then inflated to contact the expanded stent. Upon deflation of the balloon, the coating was substantially transferred to the inner surfaces of the stent, thereby filling the interstices of the stent and lining the stent with poly(acrylic acid) (see FIG. 6).

EXAMPLE 3

Lining an Intravascular Stent by Applying the Hydrogel to the Inner Surfaces of the Stent from a Infusion Balloon or Channel Balloon Delivery of a hydrogel stent lining with or without an associated drug to the inner surfaces of the stent may be accomplished via a delivery port in a catheter or via a channeled balloon. A balloon catheter having pores or channels, e.g., a channel balloon, is discussed in Wang, U.S. Pat. No. 5,254,089, and Barry, U.S. Pat. No. 5,439,466, both of which are hereby incorporated by reference. Infusion catheters which have one or more ports or openings adjacent to a balloon portion, i.e., upstream of the balloon portion relative to the direction of blood flow, can also be used to deliver the hydrogel to the inner surfaces of the stent. In this case, the hydrogel would be administered from ports or channels in close proximity to the inner surfaces of the stent to create a lining within the stent.

Inflating the balloon portion of the catheter to contact the vessel wall substantially occludes the vessel and inhibits blood flow. Inflation of the balloon also urges the stent from its compacted condition to its expanded, operative condition spanning the occluded region of the vessel and contacting the adjacent normal vessel wall. The hydrogel may then be delivered to the inner surfaces of the stent via aperatures or channels of a channeled balloon over which the stent is mounted to form a stent lining. An apparatus for delivering albumin to a stent is described in U.S. Pat. No. 5,439,446, hereby incorporated by reference. In the case of a pre-existing stent, an infusion or channel balloon is introduced into the vessel, positioned so that the ports or channels are in close proximity to the inner surfaces of the stent, and the hydrogel administered through the ports or channels to contact those surfaces to create a lining within the stent. In either case, the hydrogel exits the balloon through the apertures of the balloon surface to contact the stent proximate thereto.

EXAMPLE 4

Hydrogel Crosslinking

To minimize loss of the hydrogel coating from the balloon portion of the catheter during deployment, a hydrogel polymer may be crosslinked. The crosslinking may be physical or chemical. For example, the crosslinks may be in the form of covalent or ionic bonds or weaker interactions such as van der Waals forces and hydrogen bonds.

For example, a hydrogel polymer such as agarose or gelatin can be crosslinked via hydrogen bonds. Such hydrogels are preferably stably crosslinked at 37° C. When a balloon is positioned at the site at which the hydrogel is to be released, heat is applied to the hydrogel to disrupt the hydrogen bonds. The "melted" hydrogel is then released to the inner surfaces of a stent or the wall of a lumen upon inflation of the balloon and concomitant compression of the hydrogel against the stent or tissue. Application of heat to the hydrogel is then discontinued, the balloon is deflated, and the catheter is withdrawn from the site. The deposited hydrogel returns to body temperature, i.e., approximately 37° C., allowing the hydrogen bonds to reform. Any physiologically-compatible hydrogel with a melting temperature of greater than 37° C. can be used in this manner. Agarose is typically used at a concentration of 0.5-5%, preferably at a concentration of about 1-2%.

An alginate hydrogel polymer is reversibly crosslinked in the presence of divalent cations. For example, an alginate hydrogel can be crosslinked by contacting it with a solution of calcium gluconate. The crosslinking is reversed by contacting the hydrogel with a chelating agent. A channel balloon can be coated with a crosslinked hydrogel, delivered to a desired site, an agent which disrupts the crosslinking bonds dispensed through the channels of the balloon to contact the hydrogel and the hydrogel released from the balloon. The hydrogel can be crosslinked again after deposition onto the inner surfaces of a stent or a lumen wall, e.g., by dispensing a solution of divalent cations through the channels of the balloon to contact the deposited hydrogel.

EXAMPLE 5

Stent Lining for Treating Aneurisms

Stents have been used to treat vascular aneurisms such as aortic or intracranial aneurisms. Such stents are typically impermeable, e.g., they may be recovered with woven dacron, to prevent blood from entering and pooling in the aneurism. A problem with using an impermeable stent to treat vascular aneurisms is that blood flow to both affected and healthy regions of a blood vessel is blocked by the stent. In many cases, intracranial aneurisms occur at a point of bifurcation of healthy vessels. In such a case, it is desirable to block blood flow to or from healthy collateral vessels.

An open mesh stent, e.g., a branched stent (Nitinol Development Corporation), is deployed to the area of an aneurism. Since an open mesh stent changes the pattern of blood flow in the vessel in which it is deployed, blood may no longer enter and pool in the aneurism, obviating the need for further treatment. However, if the stent alone is not an effective treatment, a second procedure to line the stent to render it impermeable can be performed. An advantage of the stent lining method described herein is that selected areas of the stent, e.g., an area near or adjacent to an aneurism, may be lined, leaving other areas, e.g., areas of healthy tissue, areas of bifurcation, or areas in which healthy collateral vessels enter or exit, unlined. For example, a hydrogel polymer which is insoluble in blood can be delivered to the inner surface of a stent at the site of an aneurism using a balloon catheter. The polymer, e.g., poly (acrylic acid), can be delivered as a coating on a balloon portion of a catheter and released to the inner surface of a stent near or adjacent to an affected portion of the vessel by expansion of the balloon. Alternatively, a dacron patch may be adhered to a polymer coating and delivered to the aneurism site for release to the inner surface of the stent at the aneurism site.

The dacron patch itself may be coated with a polymer to facilitate its attachment to the inner surface of the stent. Thus, an open mesh stent is rendered impermeable only in the area of the polymer lining or dacron patch but remains permeable in unlined areas. As a result, the flow of blood in the lined portions of the stent is directed down the length of the stent rather than through the interstices of the stent. In unlined regions of the stent, blood can flow through the interstices of the stent, e.g., to or from collateral vessels.

Other embodiments are within the following claims.

What is claimed is:

1. A method for lining a stent, comprising:
   (a) providing a catheter assembly comprising a balloon at least a portion of which is coated with a hydrogel, wherein said hydrogel comprises a therapeutic agent selected from the group consisting of an anti-platelet drug, an anticoagulant drug, an anti-metabolite drug, an anti-angiogenic drug or an anti-proliferative drug, wherein an expansible stent is mounted on said balloon in a contracted condition,
   (b) introducing said assembly into a body lumen; and
   (c) inflating said balloon to lodge said stent in said body lumen and to release said hydrogel from said coated portion to an inner surface of said stent as a lining.

2. The method of claim 1, wherein said body lumen is a blood vessel.

3. The method of claim 2, wherein said vessel is an occluded artery.

4. The method of claim 1 wherein said hydrogel is selected from the group consisting of a polyacid, cellulosic polymer, collagen, gelatin, albumin, alginate, poly-2-hydroxy ethyl methyl acrylate (HEMA), polyvinylpyrrolidone, maleic anhydride polymer, polyamide, polyacrylamide, polyvinyl alcohol, polyethylene glycol, polyethylene oxide, and polysaccharide.

5. The method of claim 1 wherein said hydrogel is crosslinked.

6. The method of claim 5 wherein said hydrogel is poly(acrylic acid) or a polycarboxylic acid.

7. The method of claim 5 wherein said hydrogel is hyaluronic acid.

8. The method of claim 1 wherein said hydrogel is derivatized albumin.

9. The method of claim 1 wherein said hydrogel an acrylic acid.

10. The method of claim 1 wherein said hydrogel is polyanhydride.

11. The method of claim 1 wherein said catheter further comprises a sheath for covering at least a portion of said balloon which is coated with said hydrogel.

12. The method of claim 11, comprising removing said sheath prior to inflating said balloon.

13. The method of claim 1 wherein said stent is a permeable stent.

14. The method of claim 1 wherein said catheter comprises a plurality of delivery ports.

15. The method of claim 14, wherein said delivery port is located proximal to said balloon, upstream of said stent with respect to blood flow, such that hydrogel administered via said delivery port is carried by blood flow to said inner surface of said stent.

16. A method of lining a stent positioned in a body lumen, comprising:
   (a) providing a catheter comprising a balloon at least a portion of which is coated with a hydrogel, wherein said hydrogel is selected from the group consisting of a polyacid, cellulosic polymer, collagen, gelatin, albumin, alginate, poly-2-hydroxy ethyl methyl acrylate (HEMA), polyvinylpyrrolidone, maleic anhydride polymer, polyamide, polyacrylamide, polyvinyl alcohol, polyethylene glycol, polyethylene oxide, and polysaccharide, wherein the hydrogel comprises a therapeutic agent selected from the group consisting of an anti-platelet drug, an anticoagulant, an anti-metabolite drug, an anti-angiogenic agent or an anti-proliferative drug;
   (b) introducing said catheter into said body lumen;
   (c) advancing said catheter in said body lumen until said coated portion is positioned proximate to an inner surface of said stent; and
   (d) inflating said balloon to release said hydrogel from said coated portion to said inner surface of said stent as a lining.

17. The method of claim 16, wherein said body lumen is a blood vessel.

18. The method of claim 17, wherein said vessel is an occluded artery.

19. The method of claim 16, wherein said hydrogel is crosslinked.

20. The method of claim 16, wherein said hydrogel is poly(acrylic acid) or a polycarboxylic acid.

21. The method of claim 20, wherein said poly(acrylic acid) is cross-linked.

22. The method of claim 16, wherein said hydrogel is hyaluronic acid.

23. The method of claim 22, wherein said hyaluronic acid is cross-linked.

24. The method of claim 23 wherein said catheter further comprises a sheath for covering at least a portion of said balloon which is coated with said hydrogel.

25. The method of claim 24, comprising removing said sheath prior to inflating said balloon.

26. The method of claim 16, wherein said hydrogel is derivatized albumin.

27. The method of claim 16, wherein said hydrogel an acrylic acid.

28. The method of claim 16, wherein said hydrogel is polyanhydride.

29. The method of claim 16, wherein said stent is a permeable stent.

30. The method of claim 16, wherein said catheter comprises a plurality of delivery ports.

31. The method of claim 30, wherein said delivery port is located proximal to said balloon, upstream of said stent with respect to blood flow, such that hydrogel administered via said delivery port is carried by blood flow to said inner surface of said stent.

32. A method of lining a stent positioned in a body lumen, comprising:
   (a) providing a catheter comprising a balloon and a delivery port, wherein said balloon comprises a first layer and a second outer apertured layer overlying said delivery port;
   (b) introducing said catheter into said body lumen;
   (c) advancing said catheter in said body lumen until said outer apertured layer is positioned proximate to an inner surface of said stent;
   (d) delivering a hydrogel into a space between said first layer and said second outer apertured layer, wherein said hydrogel is selected from the group consisting of a polyacid, cellulosic polymer, collagen, gelatin, albumin, alginate, poly-2-hydroxy ethyl methyl acrylate (HEMA), polyvinylpyrrolidone, maleic anhydride polymer, polyamide, polyacrylamide, polyvinyl alcohol, polyethylene glycol, polyethylene oxide, and polysaccharide, wherein the hydrogel comprises a therapeutic agent selected from the group consisting of an anti-platelet drug, an anticoagulant, an anti-metabolite drug, an anti-angiogenic agent or an anti-proliferative drug; and (e) inflating said balloon to press said hydrogel through said outer apertured layer, wherein said hydrogel is deposited on said inner surface of said stent as a lining.

33. The method of claim 32, wherein said body lumen is a blood vessel.

34. The method of claim 33, wherein said vessel is an occluded artery.

35. The method of claim 32, wherein said hydrogel is crosslinked.

36. The method of claim 32, wherein said hydrogel is poly(acrylic acid) or a polycarboxylic acid.

37. The method of claim 32, wherein said poiy (acrylic acid) is cross-linked.

38. The method of claim 32, wherein said hydrogel is hyaluronic acid.

39. The method of claim 38, wherein said hyaluronic acid is cross-linked.

40. The method of claim 32, wherein said hydrogel is derivatized albumin.

41. The method of claim 32, wherein said hydrogel is an acrylic acid.

42. The method of claim 32, wherein said hydrogel is polyanhydride.

43. The method of claim 32, wherein said catheter further comprises a sheath for covering at least a portion of said balloon which is coated with said hydrogel.

44. The method of claim 43, comprising removing said sheath prior to inflating said balloon.

45. The method of claim 32, wherein said stent is a permeable stent.

46. The method of claim 32, wherein said catheter comprises a plurality of said delivery ports.

47. The method of claim 46, wherein said delivery port is located proximal to said balloon, upstream of said stent with respect to blood flow, such that hydrogel administered via said delivery port is carried by blood flow to said inner surface of said stent.

* * * * *

UNITED STATES PATENT AND TRADEMARK OFFICE
CERTIFICATE OF CORRECTION

PATENT NO. : 7,371,257 B2  Page 1 of 1
APPLICATION NO. : 10/997088
DATED : May 13, 2008
INVENTOR(S) : Sahatjian et al.

It is certified that error appears in the above-identified patent and that said Letters Patent is hereby corrected as shown below:

Column 1, line 52, "prothesis" should be changed to --prosthesis--;
Column 3, line 45, "aperatured" should be changed to --apertured--;
Column 3, line 47, "aperatured" should be changed to --apertured--;
Column 3, line 49, "aperatured" should be changed to --apertured--;
Column 6, line 55, "Poat-Deployment" should be changed to --Post-Deployment--;
Column 6, line 57, "been previously been" should be changed to --been previously--;
Claim 9, lines 1-2 (column 9, lines 44-45), "hydrogel an acrylic acid" should be changed to --hydrogel is an acrylic acid--;
Claim 27, lines 1-2 (column 10, lines 38-39), "hydrogel an acrylic acid" should be changed to --hydrogel is an acrylic acid--; and
Claim 37, lines 1-2 (column 11, lines 18-19), "poiy (acrylic acid)" should be changed to --poly (acrylic acid)--.

Signed and Sealed this

Eighth Day of September, 2009

David J. Kappos
*Director of the United States Patent and Trademark Office*